United States Patent [19]
Tran et al.

[11] Patent Number: 6,156,241
[45] Date of Patent: *Dec. 5, 2000

[54] IOLS AND PRODUCTION METHODS FOR SAME

[75] Inventors: Duc Q. Tran, Trabuco Canyon; Russell J. Lind, San Clemente, both of Calif.

[73] Assignee: Allergan, Waco, Tex.

[*] Notice: This patent is subject to a terminal disclaimer.

[21] Appl. No.: 09/223,649

[22] Filed: Dec. 30, 1998

Related U.S. Application Data

[60] Continuation of application No. 08/784,598, Jan. 21, 1997, Pat. No. 5,902,523, which is a division of application No. 08/670,679, Jun. 26, 1996, abandoned.

[51] Int. Cl.$^7$ ........................................... B29D 11/00

[52] U.S. Cl. ........................ 264/1.7; 156/73.1; 264/442

[58] Field of Search ..................... 264/1.7, 1.36, 264/1.37, 1.38, 2.7, 442, 443; 156/73.1, 272.15

[56] References Cited

U.S. PATENT DOCUMENTS

| | | |
|---|---|---|
| 3,296,161 | 1/1967 | Kulpa . |
| 3,382,205 | 5/1968 | Beers . |
| 3,994,027 | 11/1976 | Jensen et al. . |
| 4,025,965 | 5/1977 | Siegmund . |
| 4,212,719 | 7/1980 | Osada et al. . |
| 4,243,327 | 1/1981 | Dehaan et al. . |
| 4,307,043 | 12/1981 | Chase et al. . |
| 4,312,575 | 1/1982 | Peyman et al. . |
| 4,499,148 | 2/1985 | Goodale et al. . |
| 4,502,163 | 3/1985 | Graham . |
| 4,536,897 | 8/1985 | Powell . |
| 4,580,299 | 4/1986 | Lindstrom . |
| 4,609,420 | 9/1986 | Aydin et al. . |
| 4,615,702 | 10/1986 | Koziol et al. . |
| 4,619,662 | 10/1986 | Juergens, Jr. . |
| 4,660,446 | 4/1987 | Kaplan et al. . |
| 4,662,882 | 5/1987 | Hoffer . |
| 4,701,288 | 10/1987 | Cook et al. . |
| 4,702,865 | 10/1987 | Koziol et al. . |
| 4,718,905 | 1/1988 | Freeman . |

(List continued on next page.)

FOREIGN PATENT DOCUMENTS

| | | |
|---|---|---|
| 687549 | 12/1995 | European Pat. Off. . |
| 1-141705 | 6/1986 | Japan . |
| 2180757 | 4/1987 | United Kingdom . |
| 9004512 | 5/1990 | WIPO . |
| 920708 | 1/1992 | WIPO . |
| 9314924 | 8/1993 | WIPO . |

OTHER PUBLICATIONS

Chawla, A.S., Artificial Organs, vol. 3, No. 1, 1979.
Evans et al, Analytical Chemistry, vol. 51, No. 3, 1979.
Donnet et al, Carbon, vol. 24, No. 6, pp. 757–770, 1986.
Cormia et al, R & D Magazine, Jul. 1990.
Osada et al, Thin Solid Films, 118 (1994) 197–202.
Sipehia et al, Biomaterials, Nov. 1986, vol. 7.
Suzuki et al, Macromolecules, 1986, vol. 19, 1804–1808.
Sakata et al, Journal of Applied Polymer Science, 1976, vol. 20, 573–579.
Wrobel et al, Sci. Chem., A14(3), pp. 321–337 (1980).

Primary Examiner—Mathieu D. Vargot
Attorney, Agent, or Firm—Stout, Uxa, Buyan & Mullins, LLP; Frank J. Uxa

[57] ABSTRACT

New intraocular lenses (IOLs) and methods for producing IOLs. The present methods include a combination of steps which increase the pull strength between the fixation member of the IOL and the optic of the IOL without requiring sophisticated high frequency corona discharge activation or plasma activation or other exotic activation of the fixation member or primer coating of the fixation member. The silicone polymeric optic members employed in the present invention can be formed, for example, molded, without recesses to accommodate the fixation members. Such recesses can be formed and provided with a quantity of silicone polymeric material precursor composition after the optic members are produced. The fixation members are then placed in the recesses and secured to the optic members. The present methods are straight forward, easy to practice and are cost effective in producing high quality IOLs.

16 Claims, 1 Drawing Sheet

U.S. PATENT DOCUMENTS

| | | |
|---|---|---|
| 4,735,632 | 4/1988 | Hatzenbuhler . |
| 4,737,322 | 4/1988 | Bruns et al. . |
| 4,790,846 | 12/1988 | Christ et al. . |
| 4,834,751 | 5/1989 | Knight et al. . |
| 4,854,999 | 8/1989 | Schirmer . |
| 4,888,013 | 12/1989 | Ting et al. . |
| 4,936,849 | 6/1990 | Knoll et al. . |
| 5,032,209 | 7/1991 | Shinbach . |
| 5,069,926 | 12/1991 | Iwata et al. . |
| 5,080,924 | 1/1992 | Kamel et al. . |
| 5,104,590 | 4/1992 | Blake . |
| 5,126,164 | 6/1992 | Okazaki et al. . |
| 5,141,507 | 8/1992 | Parekh . |
| 5,147,397 | 9/1992 | Christ et al. . |
| 5,185,107 | 2/1993 | Blake . |
| 5,252,262 | 10/1993 | Patel . |
| 5,423,929 | 6/1995 | Doyle et al. . |
| 5,527,415 | 6/1996 | Doyle et al. . |
| 5,902,523 | 5/1999 | Tran et al. . |

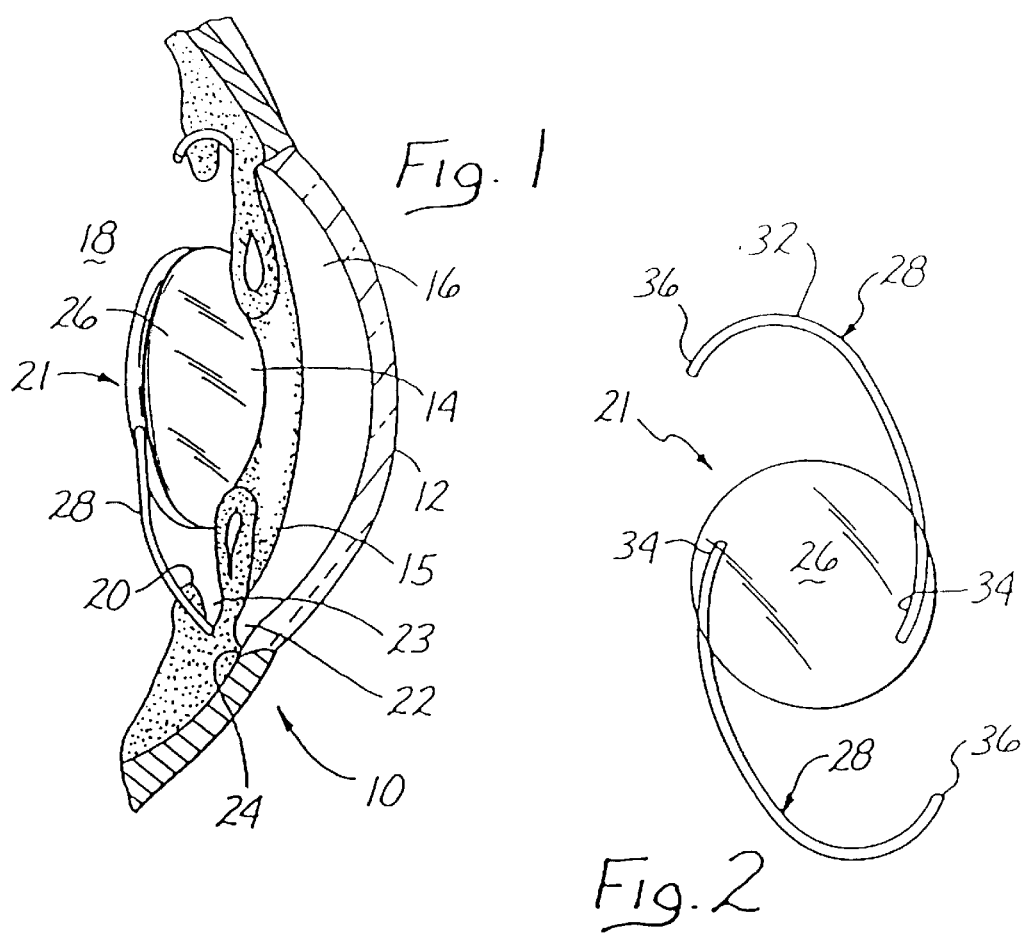
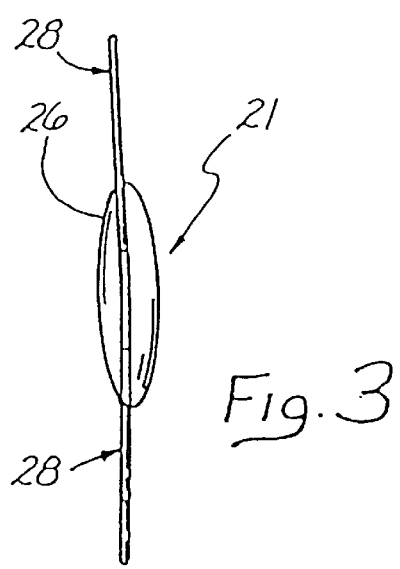

IOLS AND PRODUCTION METHODS FOR SAME

This application is a continuation of application Ser. No. 08/784,598 filed Jan. 21, 1997, now U.S. Pat. No. 5,902,523, which is a divison of application Ser. No. 08/670,679 filed Jun. 26, 1996, now abandonded.

BACKGROUND OF THE INVENTION

This invention relates to intraocular lenses (IOLs) and to methods for producing IOLs. More particularly, the present invention relates to very straight forward and easy to practice methods for producing IOLs with optics comprising silicone polymeric materials and to such IOLs which have advantageous properties, for example, outstanding fixation member pull strengths, that is advantageously large bond strengths between the optic of the IOL and the fixation member or members of the IOL.

The use of IOLs to improve vision and/or to replace damaged or diseased natural lenses in human eyes, particularly natural lenses impaired by cataracts, has achieved wide acceptance. Accordingly, a variety of IOLs has been developed for surgical implantation in the posterior or anterior chambers of the eye according to a patient's needs.

Known IOLs comprise an optical lens portion or optic which includes an optical zone, and one or more, preferably two, supporting structures, called fixation members or haptics, for contacting eye tissue to fix or hold the IOL in the proper position after implantation. The optic may comprise a soft, resilient material, such as a silicone polymeric material (in particular, an elastomeric silicone polymeric material) or a relatively hard or rigid material such as, for example, polymethylmethacrylate (PMMA). The haptics typically comprise a filament constructed of a resilient metal or polymeric substance, such as PMMA, polyimide or polypropylene.

Each of the filament haptics is preferably flexible to reduce trauma to sensitive eye structures and to be yielding during insertion of the IOL. In addition, filament haptics generally have a memory retaining capability, e.g., springiness, so that after implantation of an associated IOL, the filament haptics automatically tend to return to their normal orientation.

Although the filament haptics are very useful, certain difficulties remain. For example, filament haptics and soft or deformable optics tend to be formed from dissimilar materials which do not ordinarily chemically bond together. As a result, filament haptics have been designed having a variety of attachment end configurations or structures, e.g., anchor structures, for providing a physical or mechanical interlock between the haptic and optic. Polypropylene haptics, for example, have been secured into silicone polymer-based optics by means of a mechanical lock. This lock may comprise a small loop or other anchor formed at the attachment end or lens bonding region of the haptic, which is then placed in a mold. The precursor material of the silicone polymer-based optic is poured into the mold, through and/or around the lens bonding region of the included haptic or haptics, and is then cured. Christ et al U.S. Pat. No. 4,790,846 discloses the molding of an optic around a haptic having a small loop or other anchor to effect a secure haptic connection.

Christ et al U.S. Pat. No. 4,790,846 further discloses a method for making an IOL in which a region of an elongated filament haptic has a different configuration, e.g., a bulbous enlargement, which cooperates with the optic of the IOL to form a mechanical interlock between this different configuration and the optic. If desired, the bulbous enlargement may have its outer surface roughened to improve adhesion of the material of the optic.

Blake et al U.S. Pat. No. 5,104,590 discloses improving the adhesive properties of polypropylene haptics to silicone lenses through surface treatment of the haptic with a combination of a high frequency corona discharge and a silicone primer. Christ et al U.S. Pat. No. 5,147,397 discloses exposing the lens bonding region of the haptic to a plasma at conditions effective to enhance the bondability of the lens bonding region to the optic. While these procedures can be effective in enhancing haptic/optic bond strength, they are relatively sophisticated and are relatively expensive to practice, thus adding to the complexity and cost of producing IOLs. In addition, substantial care must be exercised in controlling the corona discharge and plasma exposing procedures to avoid damaging the relatively fine filament haptics.

Doyle et al U.S. Pat. No. 5,423,929 discloses bonding a fixation member to an optic of an IOL using a primer component coated on the fixation member. Using this system, good fixation member optic bond strengths are obtained. However, these methods do involve a step of placing a primer component on the fixation member. Also, the presence of the primer component or a residue thereof in the eye (with the final IOL) may have some potential impact on the IOL patient.

It would be advantageous to provide a more straight forward and easy to practice method of producing IOLs which effectively enhances the bond or pull strength between the fixation member or members and the optic.

SUMMARY OF THE INVENTION

New methods for producing IOLs and new IOLs have been discovered. The present production methods are very straight forward, easy to practice and cost effective, and provide IOLs which have outstanding fixation member pull strengths. Further, this high or large pull strength is achieved with little or no risk of detrimentally affecting the intrinsic strength and other advantageous properties of the fixation member in producing the IOL. It has been found that acceptably large fixation member pull strengths are achieved, preferably without requiring activation of the fixation member surface with high frequency corona discharge or plasma and without coating the fixation member surface with primer component. The present methods very reliably, predictably and reproducibly produce high quality IOLs.

In addition, since in accordance with the present invention the optic is formed prior to joining the fixation member or members to the optic, the conditions at which the optic is formed can be chosen to optimize the properties of the optic without consideration for possible damage to the relatively fine filament haptic. Also, relatively low melting point materials of construction can be used in the fixation members. Moreover, the cost of the IOL is reduced, for example, because simplified optic molding or other optic forming procedures can be employed. Increased flexibility in molding cycle time and curing temperature, and increased interchangeability in the mold tooling required for optic forming results because the fixation member is not present when the optic is being formed. This increased flexibility and interchangeability, in turn, increase production capacity and/or reduce capital and product development costs.

The present IOLs are straight forward in construction, provide for little or no interference with the optical zone of the optic by the fixation member or members and have substantial fixation member/optic pull strengths. The present IOLs are preferably produced using the present IOL production methods.

In one broad aspect, the present invention is directed to methods for producing an IOL including an optic and at least one fixation member having a proximal end or lens bonding region located in the optic. The present methods comprise forming a recess in an optic member, preferably a preformed optic member, which comprises a silicone polymeric material; placing a precursor composition of a silicone polymeric material, preferably a precursor composition of a cross-linked silicone polymeric material, into the recess; thereafter placing the proximal end portion of the fixation member into the recess; and subjecting the optic member and the fixation member in the recess to conditions effective to polymerize or cure the precursor composition. The proximal end portion of the fixation member, and preferably the entire fixation member, is preferably subjected to no high frequency corona discharge or plasma activation or other exotic activation procedure, and has no primer component coating.

In one particularly useful embodiment, the recess forming step and the precursor composition placing step occur substantially simultaneously. For example, a hollow needle-like implement is used to puncture the optic and form the recess. An amount, preferably a controlled amount, of precursor composition is passed through the hollow needle-like implement and is placed in the newly formed recess. The amount of precursor component placed in the recess is preferably controlled, more preferably automatically controlled, for example, through the use of a precision mechanism such as a micro stepper motor, a servo motor or a volumetric valve. Such control enhances the reproducibility (from lens to lens) of the present methods and facilitates the production of IOLs having very consistent haptic/optic pull strengths in excess of the current ANSI standard of 50 grams minimum.

The present methods preferably further comprise forming the optic member, for example, using a mold. The proximal end portion of the fixation member is preferably made of a non-silicon-containing material and is preferably formed with no anchor structure or structures In a more preferred embodiment, the fixation member has a length and has a substantially uniform cross-sectional area along its length. Placing the precursor composition in the recess prior to the proximal end of a fixation member, preferably which has not been subjected to high frequency corona discharge activation or plasma activation or other exotic activation procedure and has no primer coating, in combination with the other steps of the present methods, has been found to result in a very effective and straight forward approach to producing high quality IOLs with very advantageous properties.

In another broad aspect of the present invention, IOLs are provided which include an optic, and a fixation member, preferably two fixation members. The optic member comprises a silicone polymeric material, preferably which is cross-linked. The fixation member includes a proximal end portion or lens bonding region formed with no anchor structure or structures and secured in the optic. This fixation member preferably has been subjected to no high frequency corona discharge activation or plasma activation or other exotic activation procedure, and is preferably made of a non-silicon-containing material. No primer component or residue thereof is located between the fixation member and the optic. Such IOLs, which are preferably produced using the present IOL production methods, have outstanding fixation member/optic pull strengths.

The invention, together with additional features and advantages thereof may best be understood by reference to the following description taken in connection with the accompanying illustrative drawings.

BRIEF DESCRIPTION OF THE DRAWINGS

FIG. 1 is a simplified representation of the physiology of the human eye.

FIG. 2 is a plan view of an IOL in accordance with the present invention.

FIG. 3 is a side view of the IOL of FIG. 2.

DETAILED DESCRIPTION OF THE INVENTION

The present invention is based, in part, upon the discovery that the fixation member or members of an IOL can be attached or secured to the optic of the IOL with acceptably high pull strength without requiring modification to or coating of the surface of the fixation member or members. In particular, satisfactory pull strengths or fixation member or members relative to the optic of an IOL are obtained preferably without the fixation member being subjected to high frequency corona discharge activation or plasma activation and without the fixation member being coated with a primer material. Because no such surface activation or coating is required, the risk that such activation procedure or coating will affect the structure and other advantageous properties of the fixation member or members can be eliminated.

The present methods produce IOLs including an optic, which has an optical zone through which light passes so that the IOL patient has improved vision, and at least one fixation member, preferably two fixation members, having a proximal end portion or lens bonding region located in the optic.

The optic comprises a silicone polymeric material, for example, an elastomeric silicone polymeric material, which is preferably cross-linked. The optic may be, and preferably is, derived from a two part silicone formulation which is introduced into a mold cavity at a weight ratio of about 1:1, as is known to one of skill in the art. Part A typically includes a catalyst and a base polymer. Part B typically includes a cross-linker and the same base polymer. The base polymer is preferably synthesized from siloxanes. In one particularly useful embodiment, the optic comprises a polymer which is a platinum-catalyzed, vinyl/hydride, addition cured polyorganosiloxane. One particularly useful optic composition includes a silicone polymeric material which is reinforced, for example, with an effective reinforcing amount of a suitable resin and/or silica. The present optics may include one or more other components in amounts effective to provide a beneficial property to the optic. For example, an effective amount of an ultraviolet light absorbing component may be included, preferably covalently bonded to the silicone polymeric material of the optic.

The present methods of producing IOLs preferably include forming an optic member. Although other suitable techniques may be employed to form the optic member, one particularly useful approach is to form a precursor composition and inject such precursor composition into a suitable mold. The precursor-containing mold is then subjected to effective conditions, for example, conventional silicone curing conditions, to cure the precursor composition into the desired silicone polymeric material. The cured material is then removed from the mold and is ready for additional processing in accordance with the present invention of course, pre-formed optic members can be provided from other sources and, therefore, the optic member forming need not be part of the present methods.

The optic member is preferably formed with no recess or recesses for insertion of the fixation member or members. This feature, in which the optic member as formed includes no recess or recesses for the fixation member or members, greatly simplifies the procedure by which the optic member is formed. For example, in the molding approach, the mold does not have any additional wires or other means by which recesses for the fixation members are incorporated into the formed optic member. Also, since no such recesses are formed and the fixation member or members are not included during the optic member forming step, there is no concern with the fixation member or members at this point in the method. Thus, there is more flexibility in the mold cycle time and curing temperature, and more interchangeability in the mold tooling. This, in turn, increases production capacity and reduces capital, operating and other costs. Also, since the fixation member or members are not exposed to prolonged curing conditions, a wider variety of fixation member materials of construction, for example, including low melting materials or construction, can be employed.

Each fixation member typically comprises a flexible member comprising metal or, preferably, polymeric material, and has a substantially circular cross-section, although alternate cross-sectional configurations may be substituted, if desired. The cross-sectional area of the present fixation members is preferably substantially uniform along the length of the fixation member or members. The fixation members preferably have proximal end portions with no anchor structures. The fixation members have sufficient strength to provide support for the IOL in the eye. The fixation members may comprise any variety of materials which exhibit sufficient supporting strength and resilience and which are substantially biologically inert in the intended in vivo environment. Suitable materials for this purpose include, for example, polymeric materials such as polypropylene, PMMA, polycarbonates, polyamides, polyimides, polyacrylates, polyhydroxyethylmethacrylate, poly (vinylidine fluoride), polytetrafluoroethylene and the like, and metals such as stainless steel, platinum, titanium, tantalum, shape-memory alloys, e.g., nitonal, and the like. More preferably the fixation member or members comprise a polymeric material, such as those selected from polypropylene, PMMA and polyimides, especially extruded PMMA and polypropylene. The fixation members can be produced using conventional and well known forming techniques. For example, the preferred polymeric fixation members can be formed in accordance with known thermoplastic polymer forming techniques, such as by injection molding or by extrusion.

The precursor composition which is placed into the recess or recesses may be chosen from those conventionally employed in producing silicone polymeric materials, preferably cross-linked silicone-polymeric materials, for example, for use in IOLs. In a particularly useful embodiment, the precursor composition placed into the recess or recesses has substantially the same chemical make-up or composition as the precursor composition from which the optic member is formed.

As noted above, the formed optic member preferably does not include any recess or recesses into which the fixation member or members can be placed. In this circumstance, a recess or recesses is separately formed in the pre-formed or already formed optic member. Such recess or recesses have a size sufficient to accept the proximal end portion of the fixation member or members. In one embodiment, the recess forming step comprises puncturing the optic member with a needle-like implement, and removing the needle-like implement from the optic member. The needle-like implement may be coated with the above-noted precursor composition before being used to puncture the optic member. This coating facilitates the puncturing operation, and may produce a recess having a wall at least partially coated with the precursor composition.

A quantity of precursor composition is placed into the recess either during or after the recess forming step.

The recess forming step and the precursor composition placing step preferably occur substantially simultaneously. In a very effective embodiment, a hollow needle-like implement is used to puncture the optic and form the recess while a controlled amount of precursor composition is passed through the hollow needle-like implement and is placed in the recess.

The amount of precursor composition included in the recess prior to placing the proximal end portion of the fixation member into the recess preferably is sufficient to coat a major portion, that is at least about 50%, more preferably at least about 70% or about 80% and still more preferably at least about 95% or substantially all, of the outer surface of the fixation member located in the recess. Preferably, excessive amounts of precursor composition in the recess are avoided since the excess material may require an additional removal step, either before or after the precursor composition is subjected to curing or polymerizing conditions. Ideally, the amount of precursor composition placed into the recess is about equal to the void volume of the recess when the proximal end portion of the fixation member is also located in the recess.

Without wishing to limit the invention to any particular theory of operation, it is believed that having a substantial amount of precursor composition in the recess before placing the fixation member in the recess allows the precursor composition to be in intimate contact with large portions, for example, major portions, of both the inner wall of the recess and the outer surface of the fixation member located in the recess. This high degree of intimate contacting facilitates forming a strong bond between the fixation member and the optic as the precursor composition in the recess is subjected to curing or polymerizing conditions. In prior systems, the precursor composition was coated on the fixation member before it was placed in the recess. The act of placing this coated fixation member in the recess removed a substantial amount of the precursor so that relatively large portions of the outer surface of the fixation member in the recess could not be effectively bonded to the optic. The present invention overcomes this problem.

With the fixation member in place in the recess, the optic member and fixation member are subjected to conditions effective to cure or polymerize the precursor composition located in the recess. Such conditions are substantially as conventionally used to polymerize precursor compositions to form normally solid, preferably elastomeric, silicone polymeric materials. Preferably, such conditions are substantially as conventionally used to cure precursor compositions and form cross-linked silicone polymeric materials. Such conditions often include an elevated temperature, for example, in the range of about 40° C. to about 100° C. or about 150° C. However, the time during which such curing or polymerizing takes place is relatively limited because of the relatively limited amount of precursor composition present in the recess. The subjecting step preferably forms an intraocular lens assembly in which the pull strength of the fixation member is acceptable, for example, is increased, preferably by at least about 20% and more preferably by at least about 50%, relative to a similar intraocular lens assembly formed by a similar method in which the precursor composition is placed directly on the proximal portion of the fixation member and without placing the precursor composition in the recess separate from and prior to placing the fixation member in the recess.

After this subjecting step, the resulting intraocular lens assembly may be subjected to additional procedures, for example, conventional lens finishing procedures to produce the final IOL.

An additional important advantage of the present invention is the predictability and reproducibility of the present methods. Thus, in order for a method of producing IOLs to be commercially effective, the method should produce IOLs which have reliably and predictably reproducible properties, for example, to avoid the production of undue amount of waste materials and to improve cost effectiveness.

The present methods produce IOLs which preferably have fixation member/optic pull strengths with a standard deviation (defined in a conventional manner) from the mean fixation member/optic pull strength of a plurality of such IOLs produced in accordance with the present methods of less than about 15%, more preferably less than about 10%, of the mean pull strength. This outstanding predictability and reproducibility of the present methods lends itself to commercial practice since the IOLs produced have properties which have acceptable fixation member/optic pull strengths and can be reliably produced while producing reduced amount of scrap product.

Without wishing to limit the invention to any particular theory of operation, it is believed that the predictability and reproducibility of the present methods are directly linked to the straight forward and unsophisticated nature of the present methods. For example, since it is preferred that no high frequency corona discharge activation or plasma activation or primer coating of the fixation member surface be involved in the present methods, the variability which almost inherently is introduced because of such activation and coating procedures is not present in the present methods. The composition of the optic member, of the fixation member, and of the precursor composition placed in the recess, as well as the amount of precursor composition placed in the recess can be very reliably set and controlled. Also, the size of the recess in the formed optic member can be very effectively controlled. In effect, each of the steps of the present methods is relatively easy to effectively control resulting in an intraocular lens assembly which has reliable, predictable and reproducible properties.

Particularly useful silicone polymeric materials for use as optic member materials of construction are reinforced elastomeric compositions including polysiloxane elastomers, preferably having the chemical composition of a cross-linked copolymer including about 12 to about 18 mol percent of aryl substituted siloxane units of the formula $R_4R_5$—SiO where the aryl substituents ($R_4$ and $R_5$ groups) can be independently selected from phenyl groups, mono-lower alkyl substituted phenyl groups, and dilower alkyl substituted phenyl groups. Preferably, both aryl groups are simple phenyl, and the resulting diphenyl siloxane unit is present in the copolymer in an amount of about 14 to about 18 mole percent.

The copolymer is end blocked with trisubstituted (monofunctional) siloxane units. At least one substituent of the end blocking group contains an olefinic bond. Thus, the general formula of the end blocking group incorporated in the copolymer is $R_1R_2R_3SiO_{0.5}$ where the nature if the $R_1$ and $R_2$ is not critical, and they may be independently selected from, for example, alkyl, aryl, substituted alkyl and substituted aryl groups. $R_3$ contains an olefinic bond. $R_3$ is preferably an alkenyl group, more preferably a vinyl group. In a preferred embodiment, the end blocking group is a dimethyl, vinyl siloxane unit. The role of the olefinic (vinyl) group is to enable curing or cross-linking of the polymer, and preferably covalently linking certain ultraviolet light absorbing compounds to the cross-linked copolymer matrix.

The balance of the siloxane building blocks of the copolymer is preferably dialkyl siloxane units, more preferably with the two alkyl substituents being ethyl and/or methyl. In other words, the general formula of the balance of the siloxane building blocks of the copolymer is preferably $R_6R_7$—SiO where the $R_6$ and $R_7$ groups are independently selected from methyl and ethyl. Preferably both $R_6$ and $R_7$ groups are methyl.

The copolymer may have a degree of polymerization (dp) of about 100 to about 2000, although a degree of polymerization of about 250 is preferred, particularly when the $R_4$ and $R_5$ groups are phenyl and the $R_6$ and $R_7$ groups are methyl.

The preparation of the copolymer having the above described components can be performed in accordance with processes known in the art, from starting materials which are either commercially available or can be made in accordance with well known processes.

The elastomeric silicone composition preferably contains a reinforcer, for example, a fume silica reinforcer, such as trimethylsilyl treated silica reinforcer, finely dispersed therein.

The reinforcer, for example, the fume silica reinforcer, is preferably used in an amount of about 15 to about 45 parts by weight of the reinforcer to 100 parts of the copolymer. Fume silica itself is commercially available. The fume silica reinforcer preferably used has a surface area of about 100 to about 450 $meter^2/gram$. More preferably, the fume silica has a surface area of about 200 $meter^2/gram$, is present in an amount (by weight) of about 27 parts (by weight) to 100 parts (by weight) of the copolymer, and is trimethylsilylated with hexamethyldisilazane substantially in the same step where the copolymer is intimately mixed with the silica.

The intimate mixture of the fume silica with the copolymer is commonly termed the "base" in the art. For the purpose of making materials suitable for intraocular lens, the base may be dispersed in a suitable inert solvent, such as trichlorotrifluoroethane, and the dispersion filtered to remove any solid impurities. Thereafter, the solvent is removed by gentle heat and vacuum.

In accordance with standard practice in the art, the base is divided into two aliquots which preferably are of equal weight. The aliquots are commonly termed "Part A" and "Part B".

Silicon bonded hydride groups are added to the second aliquot (Part B) in the form of cross-linking agents, which are conventional and well known in the art. The liquid organohydrogen polysiloxane cross linkers having the formula $(R)_a (H)_b SiO_{4-a-b/2}$ wherein R is simple lower alkyl, for example, methyl, and a ranges from about 1.00 to about 2.10 and b ranges from about 0.1 to about 1.0, are eminently suitable.

The platinum catalyst can be selected from materials which are conventional and well known in the art.

The cross-linking should not proceed too rapidly at room temperature, thereby allowing at least two, preferably about six hours for work time with the mixed aliquots. For this reason, a suitable cross-linking inhibitor, such a 1,2,3,4-tetramethyl-1,2,3,4-tetravinyl cyclotetrasiloxane, may be added to the second aliquot (Part B)

Formation of the optic members may be accomplished by liquid injection molding, or by cast or compression molding of the intimately mixed Parts A and B. A mixture of Parts A and B, with or without the reinforcer component being present is placed in the recess or recesses formed in the molded optic member.

Referring now to FIG. 1, there is depicted in vivo placement into an eye 10 of an IOL 21 according to the present invention, in which a precursor composition was included in recesses formed in an already formed optic member prior to the lens bonding regions of the haptics being inserted into such recesses.

The cornea 12 serves as a refractory medium in addition to its function as the anterior wall of the eye 10. The pupil 14 and the iris 15 of variable aperture are located behind the cornea 12 and divide the eye into an anterior chamber 16 and a posterior chamber 18. The natural crystalline lens (not illustrated) is connected by zonular fibers to a peripheral muscle about the lens known as the ciliary muscle 20.

The surgical implantation of IOL 21 is accomplished by an incision in the eye, removal of the diseased or damaged natural lens (if applicable) and insertion of the IOL into the eye. The optic 26 of IOL 21 includes a centrally located optical zone and may be configured for implantation into a specific one or either of the anterior or posterior chambers 16 or 18. The haptics 28 of IOL 21 extend radially outwardly in the general plane of the optic 26.

A peripheral limit of anterior chamber angle 22 exists between the base of the iris 15 and a scleral spur, which serves as a support location for IOL 21 implanted within the anterior chamber 16 of the eye 10. A peripheral zone 23 also exists within the posterior chamber 18 between the ciliary muscle 20 and the base of the iris 15, which is known as the ciliary sulcus 24. The peripheral zone 23 serves as a mountain location for IOL 21 within the posterior chamber 18. Referring to FIG. 1, IOL 21 is shown positioned in the posterior chamber 18 and is supported by the haptics 28 bearing upon the ciliary sulcus 24.

Referring now to FIGS. 2 and 3, IOL 21 is illustrated as including a pair of radially outwardly extending haptics 28 secured to optic 26. The optic 26 is made of an optically clear, silica reinforced, platinum-catalyzed, vinyl/hydride addition cured (cross-linked) polyorganosiloxane polymer and has a index of refraction (refractive index) of about 1.46. Each haptic 28 has a substantially uniform cross sectional area throughout its length and is shown provided with a smoothly curved region 32, intermediate a lens bonding region 34 and a free end region 36. Although the illustrated embodiment is provided with two opposing haptics 28, it is understood that an IOL having only haptic or more than two haptics bonded to the optic by the method disclosed herein is considered within the scope of the invention.

IOL 21 is produced in accordance with the present invention, as described herein. Briefly, the optic 26 is formed, with no recesses to accommodate the haptics 28, by conventional molding techniques from a cross-linked silicone polymeric material. If desired, the lens bonding regions 34 of haptics 28 can be mechanically roughened, for example, by abrasion techniques and the like, to facilitate further increased haptic/optic bond strengths. Recesses are formed in formed optic 26 to accommodate the lens bonding regions 34 of haptics 28. Such recesses may be formed, for example, by puncturing optic 26 to an appropriate depth and at an appropriate location with a needle or a machine tool, such as a drill and the like, or by using photo ablation, ultrasound or a water jet.

Each of the recesses is formed having a size sufficient to accommodate a lens bonding region 34. If a needle is used to form the recesses, it can be coated with the precursor composition used to form the optic 26. Alternately, a pin coated with the precursor composition can be introduced into the recess to at least partially coat the walls of the recess with the precursor composition. If desired, the precursor composition can be injected into the recess. A quantity of the precursor composition used to form the optic 26 is placed in each of the recesses. The recess forming step and precursor composition placing step preferably occur substantially simultaneously using a hollow needle-like implement to puncture the optic and form the recess while passing a controlled amount of precursor composition through the hollow implement into the recess. For example, the precursor composition is introduced into the recess through the hollow implement as the implement is being withdrawn from the newly formed recess. The amount of precursor composition passed into the recess is preferably controlled using a precision device, such as a micro stepper motor, a servo motor or a volumetric valve of conventional design.

The lens bonding regions 34 of the haptics 28 are placed in such recesses and the entire assembly is subjected to silicone polymer curing conditions to secure the haptic 28 to the optic 26.

The assembled optic 26/haptics 28, which has no primer component or residue thereof between the optic and the lens bonding regions 34 and has outstanding haptic/optic pull strength, may be further processed, for example, using one or more conventional lens finishing techniques, and then packaged ready for shipment. IOL 26 may be implanted in the eye 10 using conventional techniques. After implantation, IOL 21 functions very effectively.

The present methods are very straight forward, easy and inexpensive to practice, and are effective in providing IOLs which have outstanding fixation member/optic pull strengths. Moreover, no exotic activation procedures and no primer coatings are necessary to prepare the fixation members for use in the present IOLs.

While this invention has been described with respect to various specific examples and embodiments, it is to be understood that the invention is not limited thereto and that it can be variously practiced within the scope of the following claims.

What is claimed is:

1. A method of producing an intraocular lens including an optic and at least one fixation member having a proximal end portion located in the optic, said method comprising:

placing a precursor composition of a cross-linked silicone polymeric material into a recess in an optic member comprising a silicone polymeric material; thereafter placing the proximal end portion of said fixation member into said recess, the proximal end portion of said fixation member being subjected to no high frequency corona discharge or plasma activation and having no coating of a primer component or of said precursor composition of a silicone polymeric material; and subjecting said optic member and said fixation member in said recess to conditions effective to cure said precursor composition and form a combination having a pull strength between said fixation member and said optic member in excess of 50 grams minimum.

2. The method of claim 1 wherein said fixation member is made of a non-silicon-containing material, and said placing the proximal end portion step includes placing said proximal end portion including no anchor structures into said recess.

3. The method of claim 1 wherein said precursor composition placing step occurs so as to place a controlled amount of said precursor composition in said recess.

4. The method of claim 1 wherein the chemical make-up of said precursor composition is substantially identical to the chemical make-up of the precursor composition from which said silicone polymeric material included in said optic member is formed.

5. The method of claim 1 wherein said fixation member is made of a material selected from the group consisting of polymeric materials and mixtures thereof.

6. The method of claim 1 wherein said subjecting step forms an intraocular lens assembly in which the pull strength of said fixation member is increased relative to a similar intraocular lens assembly formed by a similar method in which said precursor composition is placed directly on said proximal end portion of said fixation member and without said precursor composition placing step.

7. The method of claim 1 which further comprises roughening said proximal end portion of said fixation member, said roughening occurring prior to said proximal end portion placing step.

8. A method of producing an intraocular lens including an optic and at least one fixation member having a proximal end portion located in the optic, said method comprising:

forming a recess in an optic member which comprises a silicone polymeric material, said recess having a size sufficient to accept the proximal end portion of said fixation member;

placing a precursor composition of a cross-linked silicone polymeric material into said recess; thereafter placing the proximal end portion of said fixation member into said recess, the proximal end portion of said fixation member being subjected to no high frequency corona discharge or plasma activation and having no coating of a primer component or of said precursor composition of a silicone polymeric material; and subjecting said optic member and said fixation member in said recess to conditions effective to cure said precursor composition and form a combination having a pull strength between said fixation member and said optic member in excess of 50 grams minimum.

9. The method of claim 8 wherein said recess forming step comprises puncturing said optic member with a needle implement or a machine tool, or employing photo ablation, ultrasound or a water jet.

10. The method of claim 8 wherein said precursor composition placing step occurs so as to place a controlled amount of said precursor composition in said recess.

11. The method of claim 8 wherein said recess forming step comprises puncturing said optic member with a hollow needle implement.

12. The method of claim 11 wherein said recess forming step and said precursor composition placing step occur substantially simultaneously.

13. The method of claim 8 wherein the chemical make-up of said precursor composition is substantially identical to the chemical make-up of the precursor composition from which said silicone polymeric material included in said optic member is formed.

14. The method of claim 8 wherein said fixation member is made of a material selected from the group consisting of polymeric materials and mixtures thereof.

15. The method of claim 8 wherein said subjecting step forms an intraocular lens assembly in which the pull strength of said fixation member is increased relative to a similar intraocular lens assembly formed by a similar method in which said precursor composition is placed directly on said proximal end portion of said fixation member and without said precursor composition placing step.

16. The method of claim 8 which further comprises roughening said proximal end portion of said fixation member, said roughening occurring prior to said proximal end portion placing step.

* * * * *